US006528272B2

(12) United States Patent
Chatterjee

(10) Patent No.: US 6,528,272 B2
(45) Date of Patent: *Mar. 4, 2003

(54) RECEPTOR-BASED ASSAYS FOR PATHOGENS

(75) Inventor: Subroto Chatterjee, Columbia, MD (US)

(73) Assignee: The Johns Hopkins University, Baltimore, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/019,435

(22) Filed: Feb. 5, 1998

(65) Prior Publication Data

US 2002/0037592 A1 Mar. 28, 2002

Related U.S. Application Data

(60) Provisional application No. 60/038,145, filed on Feb. 10, 1997, and provisional application No. 60/037,553, filed on Feb. 11, 1997.

(51) Int. Cl.$^{7}$ .................................................. G01N 33/53

(52) U.S. Cl. ...................... 435/7.32; 435/7.1; 435/7.33; 435/7.37; 435/7.9; 435/7.92; 435/7.94; 435/180; 435/975; 436/518; 436/524; 436/531; 436/541; 436/808; 424/236.1; 424/243.1; 530/359

(58) Field of Search ................................. 435/7.1, 7.32, 435/7.33, 7.37, 7.9, 7.92, 7.94, 180, 975; 436/518, 524, 531, 541, 808; 424/236.1, 243.1; 530/359

(56) References Cited

U.S. PATENT DOCUMENTS

| | | | |
|---|---|---|---|
| 5,075,078 A | * 12/1991 | Osikowicz et al. |
| 5,242,800 A | 9/1993 | Jimenez et al. |
| 5,601,830 A | * 2/1997 | Su et al. |
| 5,919,665 A | * 7/1999 | Williams |
| 6,316,607 B1 | * 11/2001 | Massey et al. |

OTHER PUBLICATIONS

Ishikawa et al., Analytical Biochemistry, 231, 13–19, 1995.*

Pluskal et al., Bio Techniques, 4(3):272–283, 1986.*

Isobe et al., Analytical Biochemistry. 236. 35–40. 1996.*

Gosling, James. Enzyme Immunoassay. Immunoassay. Edited by Diamandis et al. pp. 287–308. 1996.*

D.N. Mukhin et al.: "A receptor–based immunoassay to detect Staphylococcus enterotoxin B in biological fluids" Analytical Biochemistry, vol. 245, Feb. 15, 1997, New York, NY pp. 213–217.

F. Chabraoui et al.: "Dot–blot immunodetection of antibodies against GM1 and other gangliosies on PVDF–P membranes." Journal of Immunological Methods, vol. 165, No. 2, 1993, pp. 225–230.

Chemical Absrtacts, vol. 123, No. 5, Jul. 31, 19985, Abstract No. 49588 "MultiScreen Assay System" Millipore Applications and References pp., 1–20.

Maria Jasin et al. "Glycosylphosphatidylinositol–Anchored CD4/Thy–1 Chimeric Molecules Serve as Human Immunodeficiency Virus Receptors in Human, but Not Mouse, Cells and Are Modulated by Gangliosides" Journal of Virology, Jan. 1991, pp. 440–444.

Arash Kiarash et al. "Glycosphingolipid Receptor Function is Modified by Fatty Acid Content" The Journal of Biological Chemistry, vol. 269, No. 15, pp. 11138–11146, 1994.

Subroto Chatterjee et al. "Digalactosyceramide is the receptor for staphylococcal enterotoxin–B in human kidney proximal tubular cells" Glycobiology, vol. 5, No. 3, pp. 327–333 1995.

* cited by examiner

*Primary Examiner*—Bao-Thuy L. Nguyen
(74) *Attorney, Agent, or Firm*—Banner & Witcoff, Ltd.

(57) ABSTRACT

A rapid, simple, and inexpensive sandwich enzyme-linked receptor based immunodot assay detects pathogens or pathogenic products in test samples using receptors for a characteristic component of the pathogen. This assay is widely applicable because it is highly specific, it does not require special equipment, and the results can be obtained within a few hours with the naked eye. Since the lipid-based receptors have a long-shelf life, they can be easily stored and used for a long time.

7 Claims, 7 Drawing Sheets j

RECEPTOR-BASED ASSAYS FOR PATHOGENS

CROSS REFERENCE TO RELATED APPLICATIONS

This application claims the benefit of U.S. Provisional Application No. 60/037,553, filed Feb. 11, 1997, now abandoned, and U.S. Provisional Application No. 60/038,145, filed Feb. 10, 1997, now abandoned.

The U.S. Government has a paid-up license in this invention and the right in limited circumstances to require the patent owner to license others on reasonable terms as provided for by the terms of grants awarded by the U.S. Army Medical and Research Command, under grant DAMD-17-91-Z-01027.

TECHNICAL HELD OF THE INVENTION

This invention is related to the field of analytical techniques. In particular it is related to the area of sample analysis to determine the presence of pathogens.

BACKGROUND OF THE INVENTION

Infections caused by staphylococci remain an important cause of morbidity and mortality. The virulence factors associated with the toxinogenic diseases of *Staphylococcus aureus* are the staphylococcal enterotoxins. Among them staphylococcal enterotoxin B (SEB) attracts the most attention because of its implication in immunological reactions. SEB has been shown to be able to stimulate mitogenic activity in T-cells (1). This phenomenon appears to involve specific binding of the toxin to major histocompatibility complex (MHC) class II molecules and subsequent stimulation of the T-cell via the TCR-V-beta elements (2).

Glycosphingolipids (GSL) are composed of carbohydrates, fatty acid and sphingosine. They are components of the eukaryotic cell membrane. Recently, GSL have been implicated in various biological phenomena. For example, GSL have been shown to be involved in cell proliferation (3, 4), cell migration (5, 6), and apoptosis (programmed cell death) (7). Most importantly, GSL have been shown to serve as receptors for numerous bacterial toxins and viruses (8–10). For example, a ganglioside $GM_1$, has been long established to serve as a receptor for cholera toxin (11).

We have recently shown that digalactosylceramide (diGalCer) present in the human kidney and proximal tubular cells can specifically bind SEB. It did not bind structurally related toxins, staphylococcal enterotoxin A (SEA) and toxic shock syndrome toxin-1 (TSST-1) (12). The specificity of binding to the diGalCer receptor and physiological function was established subsequently. We found that SEB induced the uptake of [$^{14}$C]choline and increased the synthesis of phosphatidylcholine, in contrast SEA and TSST-1 failed to stimulate phospholipid biosynthesis (13).

There is a need in the art for improved assays for detecting pathogens which can be used outside of laboratories in the absence of sophisticated equipment.

SUMMARY OF THE INVENTION

It is an object of the present invention to provide a method for assaying a test sample for the presence of a pathogen.

It is another object of the present invention to provide a method for assaying a test sample for the presence of a toxin.

It is an object of the present invention to provide a method for assaying a test sample for the presence of Staphylococcal enterotoxin-B.

It is another object of the invention to provide a kit for detecting Staphylococcal enterotoxin-B.

It is still another object of the invention to provide a kit for detecting a bacterial pathogen in a sample.

It is another object of the invention to provide a method for assaying for lymphocytes, neutrophils, or platelets.

It is another object of the invention to provide a method for assaying for cancer cells, including colon carcinoma and Burkitt's tumor.

These and other objects of the invention are achieved by providing one or more of the embodiments described below. In one embodiment a method for ansaying a test sample for the presence of a pathogen is provided. The method comprises the steps of:

- applying a glycosphingolipid to a polyvinylidene difluoride (PVDF) surface; wherein the glycosphingolipid is a receptor for a characteristic component of the pathogen; wherein the glycosphingolipid specifically binds the characteristic component;
- applying a liquid reaction medium comprising the test sample to the PVDF surface;
- removing excess liquid medium from the PVDF surface;
- incubating the PVDF surface with an antibody which specifically binds to the characteristic component;
- detecting the presence of the antibody on the PVDF surface, wherein the presence of the antibody indicates the presence of the characteristic component in the test sample.

According to another aspect of the invention a method is provided for assaying a test sample for the presence of a toxin. The method comprises the steps of:

- applying a protein to a PVDF surface; wherein the protein is a receptor for the toxin, wherein the protein specifically binds the toxin;
- applying a liquid reaction medium comprising the test sample to the PVDF surface;
- removing excess liquid medium from the PVDF surface;
- incubating the PVDF surface with an antibody which specifically binds to the toxin;
- detecting the presence of the antibody on the PVDF surface, wherein the presence of the antibody indicates the presence of the toxin in the test sample.

According to still another aspect of the invention, a method is provided for assaying a test sample for the presence of a Staphylococcal enterotoxin-B. The method comprises the steps of:

- applying digalactosylceramide to a PVDF surface;
- applying a liquid reaction medium comprising the test sample to the PVDF surface;
- removing excess liquid medium from the PVDF surface;
- incubating the PVDF surface with an antibody which specifically binds to Staphylococcal enterotoxin-B;
- detecting the presence of the antibody on the PVDF surface, wherein the presence of the antibody indicates the presence of Staphylococcal enterotoxin-B in the test sample.

In yet another embodiment of the invention a kit is provided for the detection of a pathogen. The kit comprises:

a PVDF surface;

a purified sample of a glycosphingolipid which specifically binds to a characteristic component of the pathogen;

an antibody which specifically binds to the characteristic component of the pathogen.

In yet another embodiment of the invention a kit is provided for the detection of Staphylococcal enterotoxin-B. The kit comprises:

a PVDF surface;

a purified sample of digalactosylceramide;

an antibody which specifically binds to Staphylococcal enterotoxin-B.

According to yet another aspect of the invention a method is provided for assaying a test sample for lymphocytes, neutrophils, or platelets. The method comprises the steps of:

applying a glycoprotein to a PVDF surface; wherein the glycoprotein is selected from the group consisting of L-selectin, E-selectin, and P-selectin;

applying a liquid test medium which may comprise neutrophils, lymphocytes, or platelets to the PVDF surface;

removing excess liquid medium from the PVDF surface after incubation;

incubating the PVDF surface with an antibody which specifically binds to the glycoprotein;

detecting the presence of the antibody on the PVDF surface, wherein the presence of the antibody indicates the presence of neutrophils, lymphocytes, or platelets in the test sample.

In another aspect of the invention a method for assaying a test sample for the presence of colon carcinoma is provided. The method comprises the steps of:

applying a test sample to a PVDF surface, wherein the test sample comprises a biopsy of suspected colon carcinoma, a lipid extract of said biopsy, or a urine sample of a patient suspected of having colon carcinoma;

washing the PVDF surface to remove components which do not bind;

incubating the PVDF surface with an antibody which specifically binds to digalactosylceramide;

detecting the presence of the antibody on the PVDF surface, wherein the presence of the antibody indicates the presence of colon carcinoma in the patient who provided the test sample.

According to another aspect of the invention a method for assaying a test sample for the presence of Burkitt's tumor is provided. The method comprises the steps of:

applying a test sample to a PVDF surface, wherein the test sample comprises a biopsy of suspected Burkitt's tumor, a lipid extract of said biopsy, or a urine sample of a patient suspected of having Burkitt's tumor;

washing the PVDF surface to remove components which do not bind;

incubating the PVDF surface with an antibody which specifically binds to globotriosylceramide;

detecting the presence of the antibody on the PVDF surface, wherein the presence of the antibody indicates the presence of Burkitt's tumor in the patient who provided the test sample.

The present invention thus provides the art with an assay which is widely applicable because it is highly specific, it does not require special equipment, and the results can be obtained within few hours with the naked eye. Moreover, since the glycosphingolipid receptors have a long-shelf life, they can be easily stored and used for a long time. In addition, the use of non-radioactive reagents renders this assay safer and more widely applicable.

DETAILED DESCRIPTION

Figure 1:
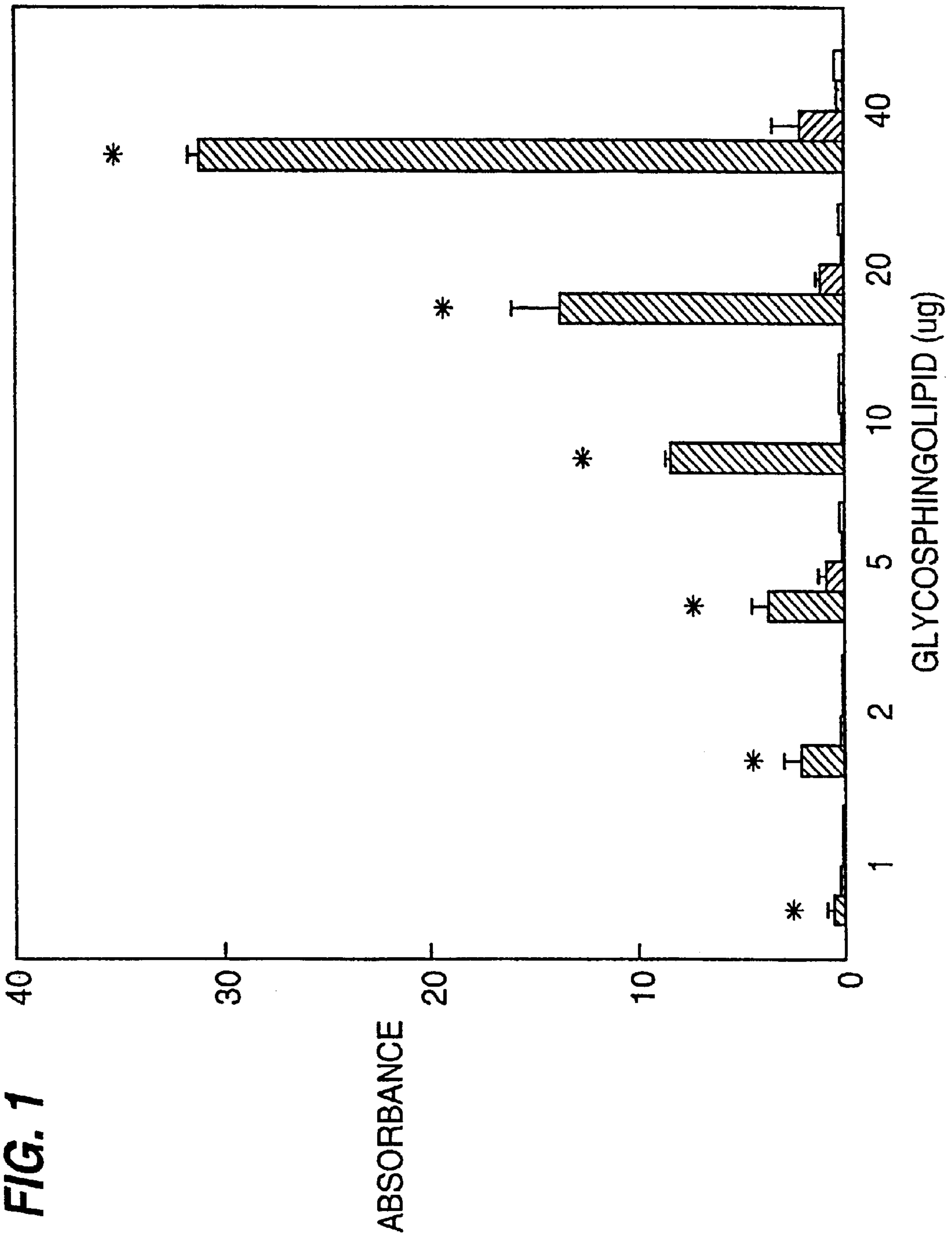
FIG. 1. Specificity of binding of SEB (1 $\mu$g/ml in PBS) versus control (no SEB) to various glycosphingolipids. MAB 12B at a dilution of 1:1,000 was employed. ▮, diGalCer; ▭, GlcCer; X, GalCer; , LacCer. Values are the mean of three experiments ±SD. *, Significant difference from control, P<0.05 (Student's t-test).

It is a discovery of the present inventor that PVDF surfaces provides an excellent substrate for receptor binding assays. PVDF membranes or PVDF-coated plates may, for example, be used for such assays.

Receptor-binding assays are those which involve the use of a receptor ligand pair. Typically these have a minimum dissociation constant of $10^{-9}$ M. Preferably the dissociation constant is greater than $10^{-10}$ M and more preferably greater than $10^{-12}$ M. The receptors can be glycosphingolipids, other lipids, glycoproteins, or proteins. Nucleic acids may also be used. The specificity of the receptor-ligand binding is increased in the assay of the present invention by using antibodies as well. Thus the receptors are bound to the PVDF surface, which in turn binds to the analyte, which in turn is bound by one or more antibodies.

According to one aspect of the invention the analyte is a characteristic component of a pathogen. This can be a part of the pathogen, such as a particular structural protein, or a product which the pathogen makes, such as a toxin. Bacterial toxins which can be tested include Vibrio cholera toxin, Staphylococcal enterotoxin-B, Staphylococcal enterotoxin-A, verocytotoxin-2, Shigella toxin, Shiga toxin, botalinum toxin, and tetanus toxin. Whole bacterial cells or viruses can also be detected using their particular receptor molecules.

Another unexpected and useful aspect of the present invention is that the specificity of the assay is so great that an analyte can be detected even in the presence of complex biological mixtures. Thus the other components present in urine, serum, biopsies, tissue extracts, or food do not prevent the use of the assay to yield practical results.

The receptors can be attached to the PVDF surface simply by application in solution or suspension and drying. A liquid reaction medium can be applied to the surface for example by flowing through the surface, by submerging the surface, or by applying a small volume to the surface. Removal of the excess liquid after an incubation period to allow the binding of the analyte to the receptor can be accomplished by any means known in the art, including gravity, vacuum, rinsing, etc.

Primary antibodies can be used for the detection of analyte attached to the surface of the PVDF surface. The primary antibodies bind to the analyte and can be monoclonal or polyclonal. A secondary antibody can be used to detect the primary antibody. The secondary antibody typically is labeled with an enzyme and has specificity for the primary antibody. The enzyme can be used in a colorimetric or fluorimetric reaction, for example, to produce a visually detectable product. Such secondary antibodies and visually detectable products are known in the art, and any suitable set can be used.

Kits are provided here, which comprise components in a package for ready usage in the assay according to the invention. Typically, written instructions to practice the methods of the invention will also be provided. The kits may include antibodies, PVDF surfaces, purified samples of the receptor(s), and samples of the analyte for use as a positive control. Suitable buffers for diluting or reconstituting test samples, antibodies or receptors may also be provided. Some of the components may be provided in dry form, and may require reconstitution. The receptors may be prebound to the PVDF surfaces. The surfaces may be divided up into any geometric shape or size. They may be provided in reaction vessels, such as in microtiter dishes.

According to another aspect of the invention, the characteristic expression of certain tumors of glycosphingolipids can be used diagnostically. A sample of the tumor can be applied to a PVDF surface. The sample can be a biopsy, such as a lysate of a biopsy, a lipid extract of a biopsy, or a urine or stool sample of a person suspected of carrying such a tumor. The test sample can be applied to the PVDF surface and, if present, the glycosphingolipids will bind. The binding can be detected by an antibody specific for the glycosphingolipid. In the case of colon carcinoma the glycosphingolipid is digalactosylceramide. In the case of Burkitt's tumor the glycosphingolipid is globotriosylceramide. Other tumors can be similarly tested if there is a characteristic expression of a glycosphingolipid associated with it.

The above disclosure generally describes the present invention. A more complete understanding can be obtained by reference to the following specific examples which are provided herein for purposes of illustration only, and are not intended to limit the scope of the invention.

EXAMPLE 1

This example demonstrates the specificity of binding of SEB to digalactosyl ceramide.

We have determined the specificity of binding of SEB to diGalCer and structurally related GSL, such as glucosylceramide (GlcCer), galactosylceramide (GalCer), and lactosylceramide (LacCer). The chemical structure of these GSLs is summarized in Table 1. We have used a MAB 12B at a dilution 1:1,000. As shown in FIG. 1, SEB at a concentration of 1 μg/ml did not significantly bind to GlcCer, GalCer, and LacCer but produced strong binding to diGalCer. These results confirm our previous report on the binding of [$^{125}$I] SEB to various glycosphingolipids immobilized on a microtiter plate (12).

EXAMPLE 2

This example demonstrates the effect of antibody dilution on the immunodetection of SEB.

Figure 2:
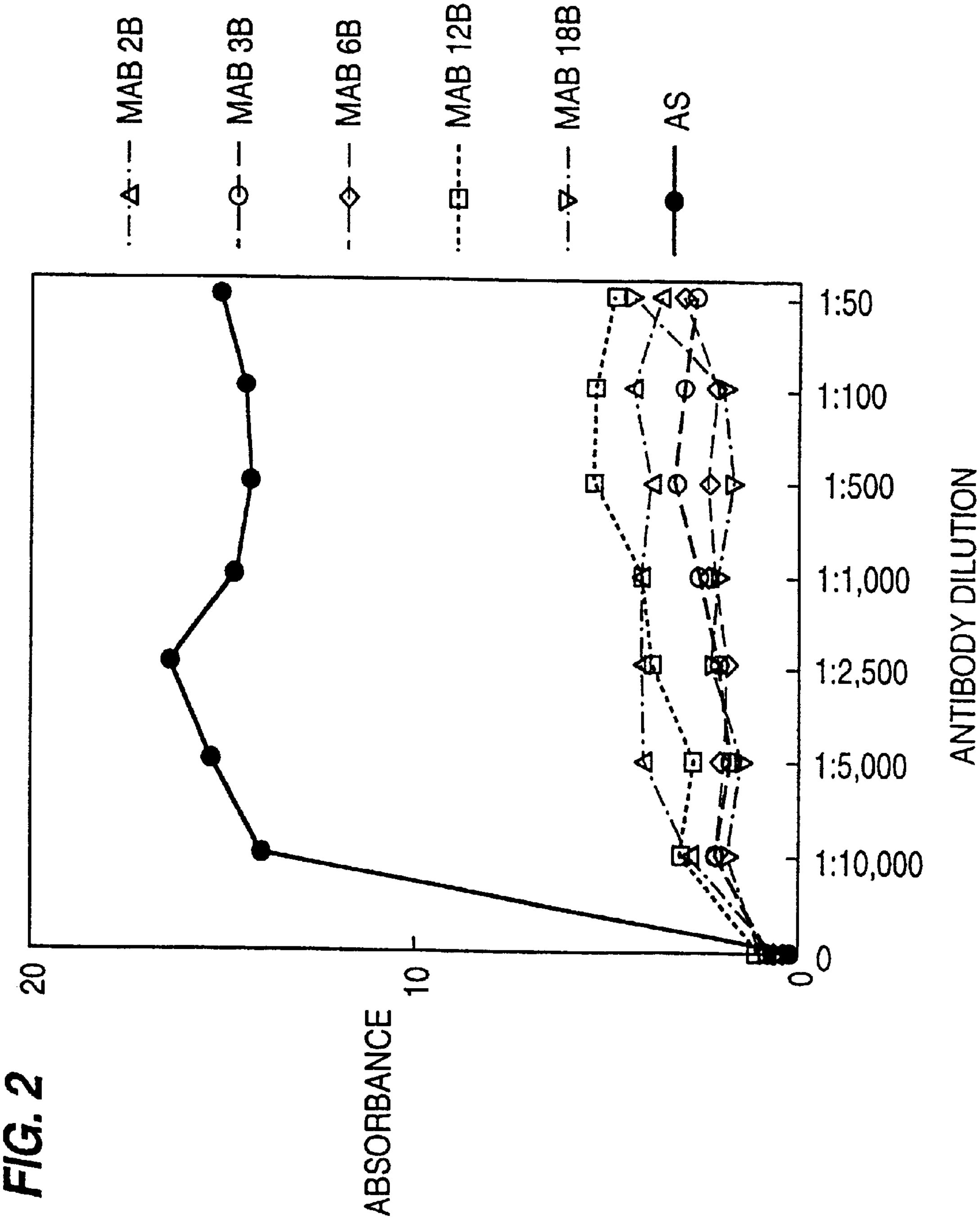
FIG. 2. Effect of antibody dilution on the immunodetection of SEB (1 $\mu$/ml in PBS). The amount of diGalCer was 3 $\mu$g.

The effect of an antibody dilution on the immunodetection of SEB is shown in FIG. 2. Polyclonal anti-SEB AS even at a dilution 1:10,000 was much more sensitive (7-folds) than the monoclonal antibodies in detecting SEB.

Figure 3:
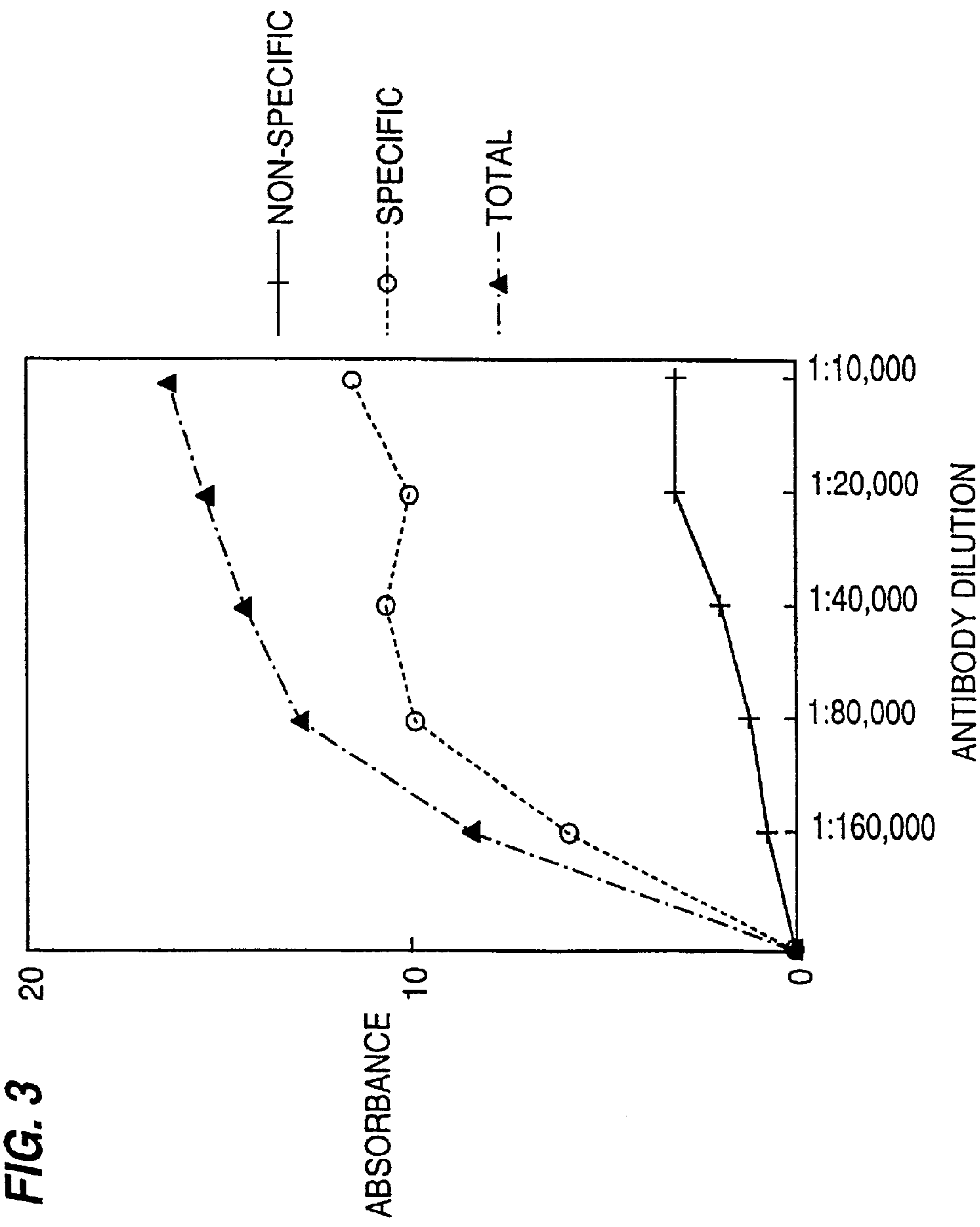
FIG. 3. Binding of different dilutions of anti-SEB AS to the complex diGalCer-SEB (total) versus diGalCer alone (non-specific). Specific curve was obtained by subtraction of "non-specific" values from "total" values.

Polyclonal anti-SEB AS obtained from a commercial source bound to the complex diGalCer-SEB (concentration of SEB was 1 μg/ml) in a saturable fashion. However, non-specific binding of anti-SEB AS to diGalCer (10 μg) in this assay increased with increase in the concentration of the AS (FIG. 3). Accordingly, in subsequent studies we have chosen the AS dilution of 1:40,000 to decrease the non-specific binding and at the same time to retain sensitivity. Similarly, we have determined that the minimal concentration of diGalCer that retains the sensitivity but eliminates nonspecific binding of AS (at the dilution 1:40,000) is 3 μg per assay.

EXAMPLE 3

This example compares the detection of different concentrations of SEB with monoclonal antibody (diluted 1:1,000) and polyclonal antiserum (diluted 1:40,000).

Figure 4:
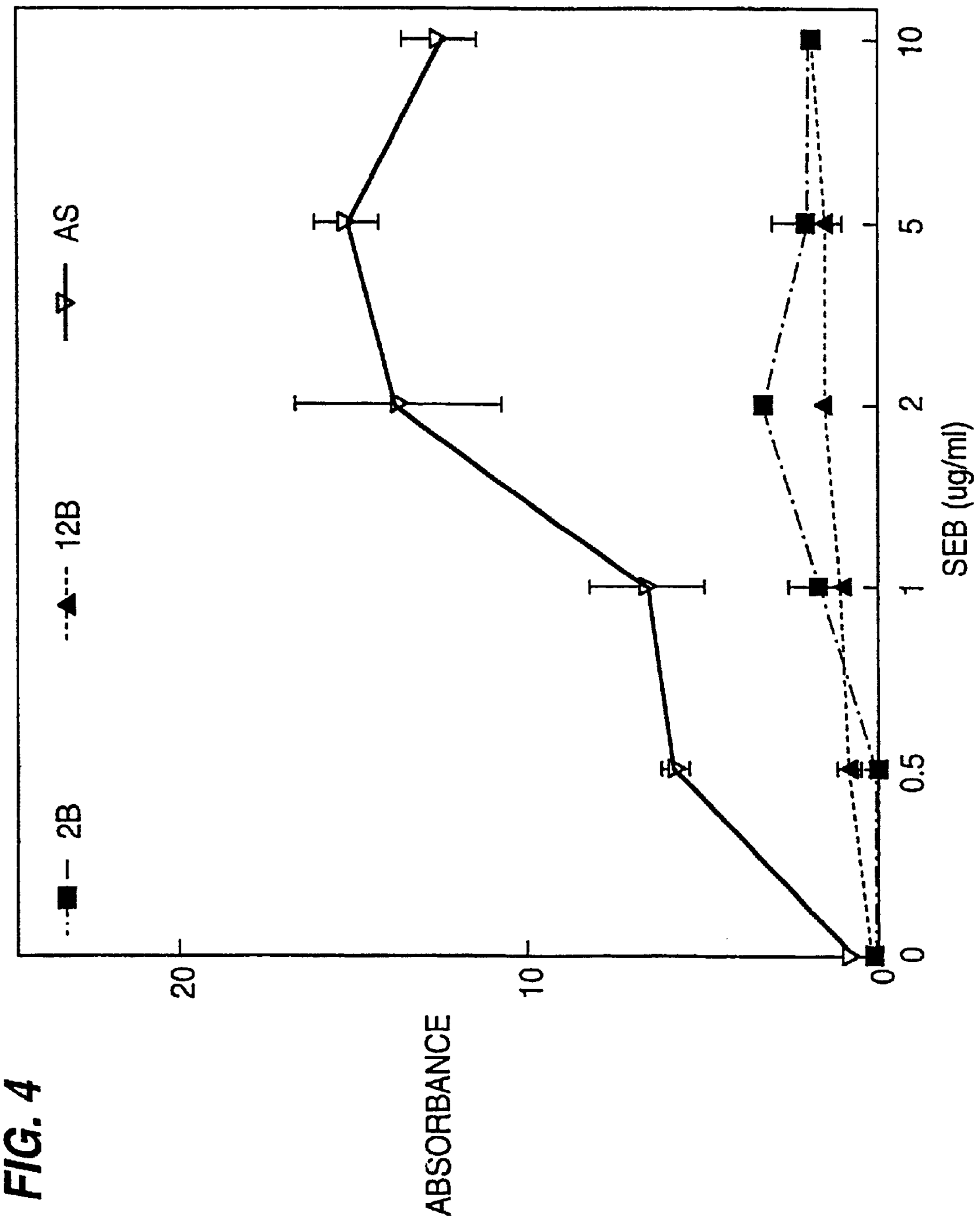
FIG. 4. Immunodetection of different amounts of SEB with monoclonal antibodies 2B, 12B (1:1,000), and antiserum (1:40,000). Values are the mean of three experiments ±SD.

We found that the commercial anti-SEB AS is most sensitive in the assay at all concentration ranges of SEB (FIG. 4). However, at higher concentrations of SEB (2 μg/ml), it is feasible to use MAB when a definitive result on the nature of intoxication is desired.

EXAMPLE 5

This example demonstrates that the assay system is highly specific.

Figure 5:
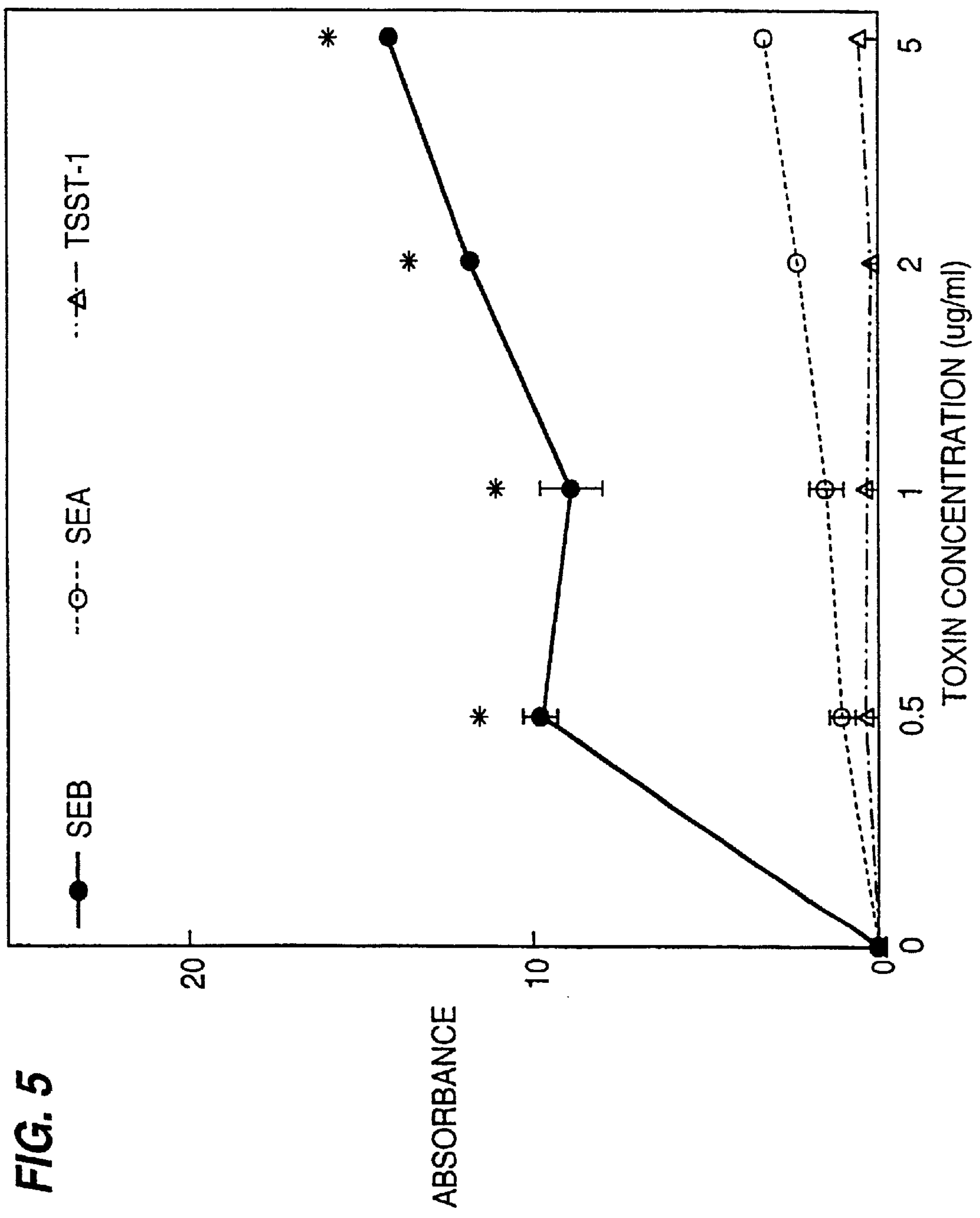
FIG. 5. Immunodetection of structurally related toxins in spiked PBS with anti-SEB AS after binding to diGalCer (3 $\mu$g). Values are the mean of three experiments ±SD. *, Significant difference from SEA, P<0.05 (Student's t-test).

We assessed the possible interference of structurally related toxins, SEA and TSST-1 with our assay employing diGalCer and commercial anti-SEB AS. At low concentrations (0.5–1 μg/ml), SEA and TSST-1 could not be detected in our assay (FIG. 5). Only at very high concentrations of SEA (>1 μg/ml) it could be non-specifically detected in the assay. These findings suggest that our assay may be suitable for use in detecting SEB in samples contaminated with other structurally related toxins. However, for samples containing high concentrations of SEA (>1 μg/ml) and a low concentration of SEB (<0.1 μg/ml) an alternative method may be recommended. Nevertheless, present results are consistent with our previous reports demonstrating that SEA and TSST-1 did not compete for binding with SEB in our microtiter plate assay and in cultured human kidney proximal cells (12). The latter was accompanied by a marked stimulation of phosphatidylcholine synthesis by SEB but not by SEA and TSST-1 (13).

EXAMPLE 6

This example demonstrates that other components of biological fluids do not interfere with detection by the assay.

Figure 6:
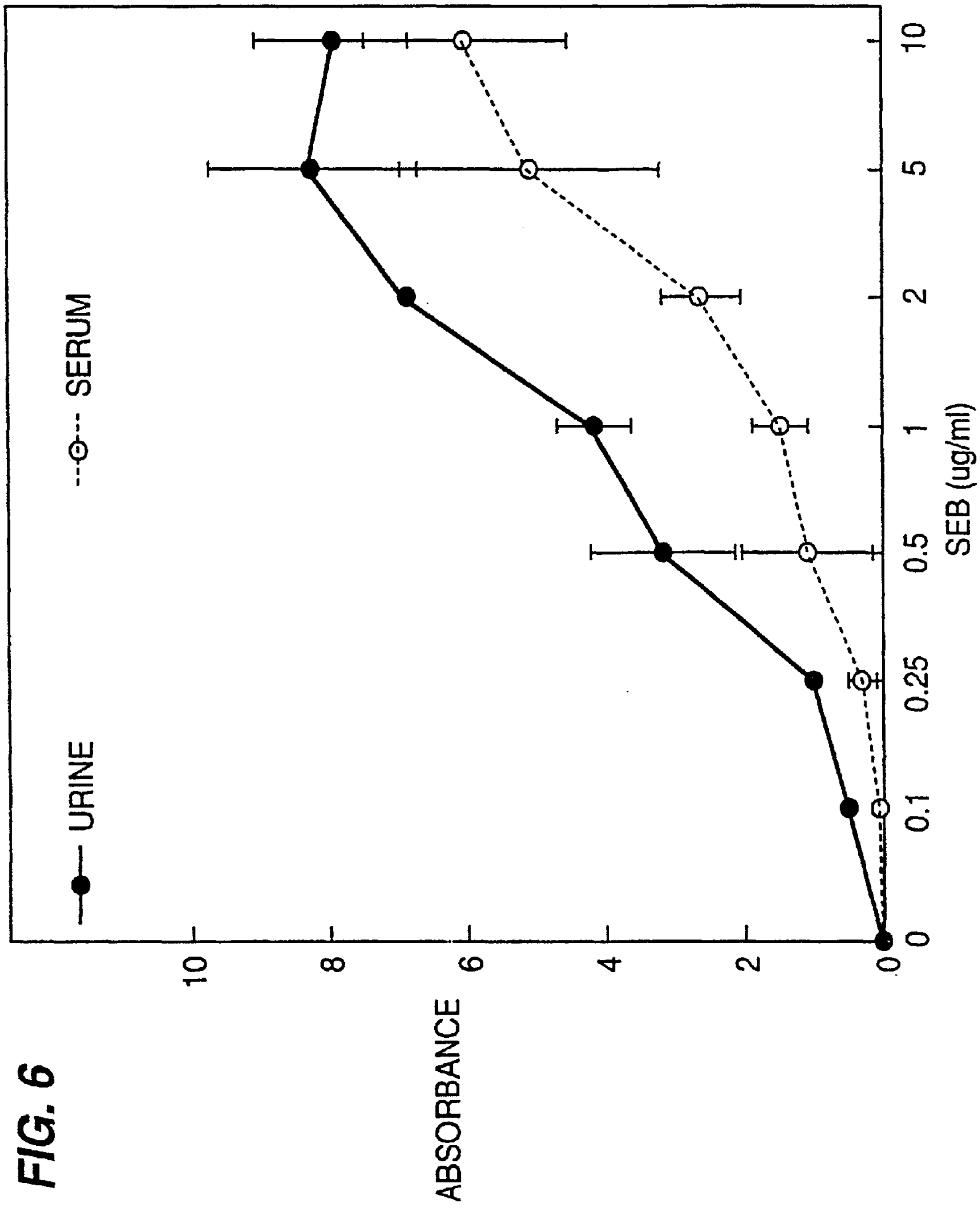
FIG. 6. Immunodetection of SEB either in spiked urine or in spiked serum with anti-SEB AS. Values are the mean of three experiments ±SD.
Figure 7:
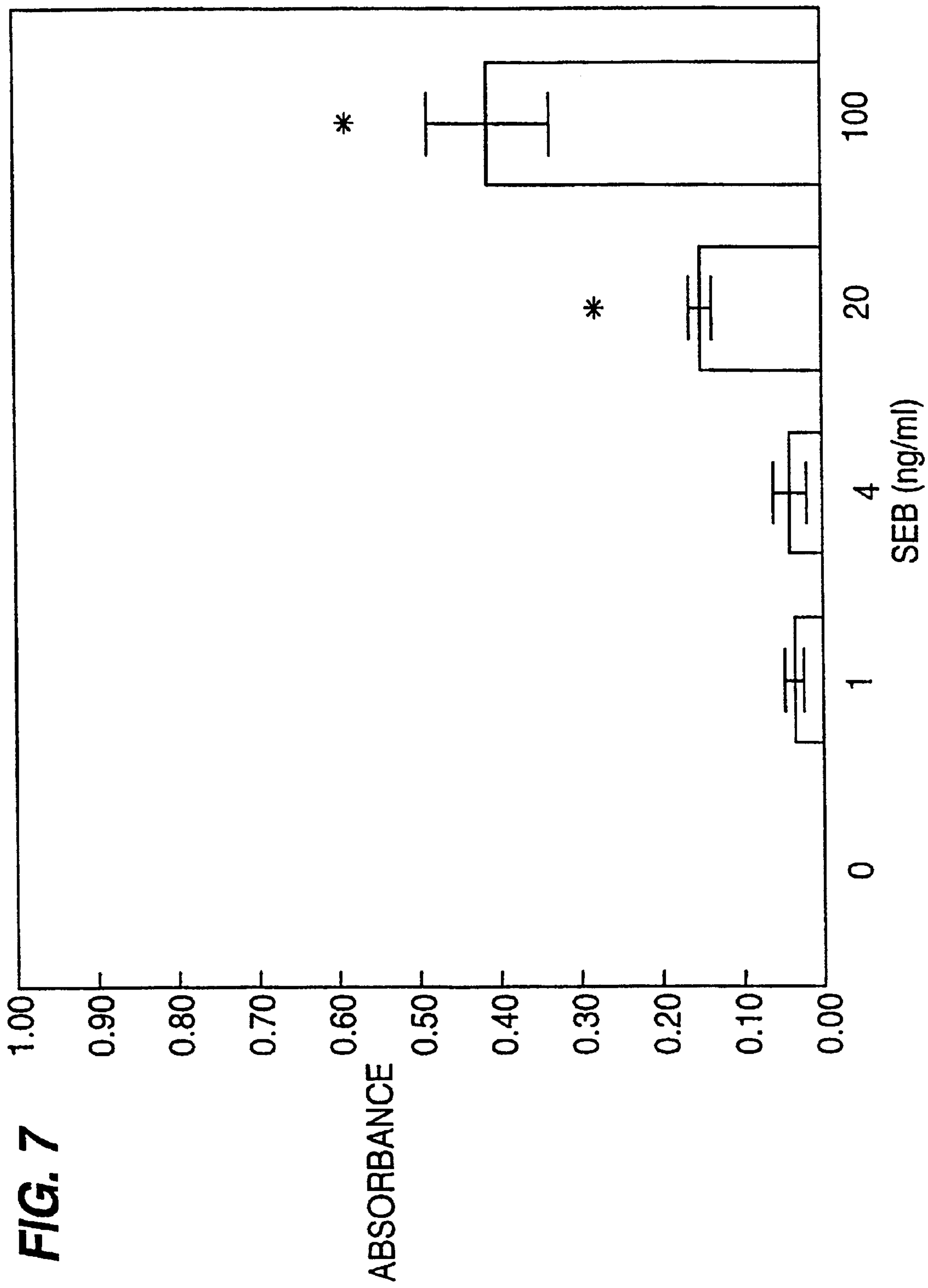
FIG. 7. Immunodetection of SEB in spiked urine with anti-SEB AS. Values are the mean of three experiments ±SD. *, Significant difference from control (no SEB), P<0.05 (Student's t-test).

To study the possibility of measuring SEB with commercial anti-SEB AS in mammals biological fluids we used human urine and serum spiked with SEB (100–10,000 ng/ml). The detectability of SEB in biological fluids was lower than in PBS. The concentration of SEB that could be detected in the serum in our assay was 500 ng/ml. At the same time 100 ng of SEB per ml in the spiked urine could be easily detected with anti-SEB AS (FIG. 6). The recovery of the enterotoxin from spiked urine was about 80% of the amount added compared with spiked PBS. Subsequently, we found that as little as 1 ng/ml of SEB in spiked urine was detectable employing our assay (FIG. 7). However, 20 ng of SEB per milliliter of urine was the lowest amount measured that was statistically significant. In the case of very low concentrations of toxin, an overnight incubation with primary anti-SEB antibodies may improve the sensitivity of the assay (data are not shown).

Our experiments do not explain why the sensitivity of the assay for SEB in human urine is higher than in human serum. A possible reason may be that serum has a number of lipid binding proteins which adsorb nonspecifically to diGalCer (such as albumin) thus preventing it from interacting with SEB.

In conclusion, various procedures have been developed to detect staphylococcal enterotoxins in food (14–21). Such methods employ microslide immunodiffuision assay, passive and reversed passive hemagglutination or latexagglutination assay, radioimmunoassay, enzyme-linked immunosorbent assay, and skin test assay. However, such studies have often suffered from nonspecific binding (22). Our assay is designed to specifically capture SEB to its receptor followed by immunodetection. Our method is a fast, simple, and inexpensive immunodot assay to detect specifically SEB in biological fluids. This analysis does not require special equipment and the results can be obtained within few hours with the naked eye. The minimal sensitivity of the assay for SEB (1 ng/ml) is comparable to that of existing tests (23).

EXAMPLE 7

This example provides the materials and methods useful in the practice of the present invention.

Materials

Polyvinyledene difluoride (PVDF) membrane was obtained from Millipore Corp., Bedford, Mass. SEB, SEA, TSST-1 and monoclonal mouse anti-SEB antibodies (MAB), clone 2B, 3B, 6B, 12B, and 18B were obtained as a gift from Drs. Peter Gemski and Marti Jett, Washington, D.C. SEB and SEA preparations were free of contaminants with other toxins, for example, lipopolysaccharides, lipid A. Upon gel-electrophoresis SEB resolved as a single band having a molecular weight on the order of about 30 kDa. Anti-mouse and anti-rabbit alkaline-labeled polyclonal antibodies were from Boehringer Mannheim Corp., Indianapolis, Ind. Bovine serum albumin (initial fractionation by heat shock) was from Sigma Chemical Company, St. Louis, Mo. Rabbit anti-SEB antiserum (AS) and other chemicals were also obtained from Sigma Chemical Company. Digalactosylceramide (diGalCer) was prepared from human Fabry kidney and characterized as described previously (12).

Immunodot Blot Assay

The following procedure for the detection of SEB on PVDF membrane has been developed. Three micrograms of diGalCer dissolved in chloroform-methanol (2:1) was applied to 4 mm diameter spots on PVDF membrane and dried at room temperature. Pieces of the membrane were placed to the wells of 96-microtiter plate and were incubated for 30 min in a 3% solution of bovine serum albumin (BSA) in phosphate-buffered saline (PBS) at room temperature. Then it was washed three times with PBS and incubated in 400 μl of PBS spiked with SEB for 60 min at room temperature (all following incubations were performed in the volume of 400 μl). The membrane was washed three times with PBS and once with 3% BSA in PBS for 10 min. After washing it was incubated with primary antibodies (anti-SEB diluted 1:40,000 or MAB diluted 1:1,000 with 3% BSA in PBS) for two hours at room temperature. Then the membrane was washed 3 times with PBS and once with 3% BSA, and was incubated with alkaline phosphatase-labeled antibodies (diluted 1:1,000 with 3% BSA in PBS) for 2 h at room temperature. After washing it was incubated in the solution of alkaline phosphatase substrate (100 mM Tris-HCl, 100 mM NaCl, 5 mM $MgCl_2$, pH 9.5; 5-bromo-4-chloro-3-indolyl-phosphate (BCIP); 4-nitro blue tetrazolium chloride (NBT); 300:2:1) for 10 min in the dark. Reaction was stopped by washing with water.

Quantitation of Results

The quantitative comparison of staining was performed by scanning densitometry on a Protein DNA Imager (PDI Inc., Huntington Station, N.Y.) equipped with image processing software.

TABLE 1

Structure of glycosphingolipids used in this study.

| Glycosphingolipid | Structure |
|---|---|
| Glucosylceramide | Glcβ1-1Cer |
| Galactosylceramide | Galβ1-1Cer |
| Lactosylceramide | Galβ1-4Glcβ1-1Cer |
| Digalactosylceramide | Galα1-4Galβ1-1Cer |

REFERENCES

1. Peavy, D. L., Adler, W. H., and Smith, R. T. (1970) *J. Immunol.* 105, 1453–1458.
2. Fleischer, B., Gerardy-Schahn, R., Metzroth, B., Carrel, S., Gerlach, D., and Kohler, W. (1991) *J. Immunol.* 146, 11–17.

3. Bhunia, A. K., Han, H., Snowden, A., and Chatterjee, S. (1996) *J. Biol. Chem.* 271, 10660–10666.
4. Shayman, J. A, Deshmukh, G. D., Mahdiyoun, S., Thomas, T. P., Wu, D., Barcelon, F. S., and Radin, N. S. (1991) *J. Biol. Chem.* 266, 22968–22974.
5. De Cristan, G., Morbidelli, L., Alesandri, G., Ziche, M., Cappa, A. P., and Gullino, P. M. (1990) *J. Cell. Physiol.* 144, 505–510.
6. Panjwani, N., Michalopoulos, G., Song, J., Zaidi, T. S., Yogeeswaran, G., and Baum, J. (1990) *Invest. Ophthalmol. Vis. Sci.* 31, 689–695.
7. Koike, T., Fehsel, K., Zielasek, J., Kolb, H., and Burkart, V. (1993) *Immunol. Lett.* 35, 207–212.
8. Angstrom, J., Teneberg, S., and Karlsson, K. A. (1994) *Proc. Natl. Acad. Sci. USA* 91, 11859–1863.
9. Cook, D. G., Fantini, J., Spitanik, S. L., and Gonzalez-Scarano, F. (1994) *Virology* 201, 206–214.
10. Muthing, J., and Unland, F. (1994) *Glycoconjugate J.* 11, 486–492.
11. Van Heyningen, S. (1974) *Science* 183, 656–657.
12. Chatterjee, S., Khullar, M., and Shi, W. Y. (1995) *Glycobiology* 5, 327–333.
13. Khullar, M., and Chatterjee, S. (1995) *Mol. Cell. Biochem.* 146, 115–120.
14. Casman, E. P., and Bennet, R. W. (1965) *Appl. Microbiol.* 13, 181–189.
15. Johnson, H. M., Bukovic, J. A., and Kauffmann, P. E. (1973) *Appl. Microbiol.* 26, 309–313.
16. Johnson, H. M., Hall, H. E., and Simon, M. (1967) *Appl. Microbiol.* 15, 815–818.
17. Morse, S. A., and Mah, R. A. (1967) *Appl. Microbiol.* 15, 58–61.
18. Read, R. B. Jr., Pritchard, W. L., Bradshaw, J., and Black, L. A. (1965) *J. Dairy Sci.* 48, 411–419.
19. Salomon, L. L., and Tew, R. W. (1968) *Proc. Soc. Exp. Biol. Med.* 129, 539–542.
20. Saunders, G. C., and Barlett, M. L. (1977) *Appl. Environ. Microbiol.* 34, 518–522.
21. Scheuber, P. H., Mossmann, H., Beck, G., and Hammer, D. K. (1983) *Appl. Environ. Microbiol.* 46, 1351–1356.
22. Park, C. E., Akhtar, M., and Rayman, M. K. (1992) *Appl. Environ. Microbiol.* 58, 2509–2512.
23. Morissette, C., Goulet, J., and Lamoureux, G. (1991) *Appl. Environ. Microbiol.* 57, 836–842.

I claim:

1. A method for assaying a test sample for the presence of Staphylococcal enterotoxin-B, comprising the steps of:

applying digalactosylceramide to a PVDF surface;

applying a liquid reaction medium comprising the test sample to the PVDF surface;

removing excess liquid medium from the PVDF surface;

incubating the PVDF surface with a first antibody which specifically binds to Staphylococcal enterotoxin-B;

detecting the presence of the first antibody on the PVDF surface, by observing a label on the first antibody or a labeled second antibody which recognizes said first antibody; wherein the presence of the first antibody indicates the presence of Staphylococcal enterotoxin-B in the test sample.

2. The method of claim 1 wherein the antibody is detected by a labeled secondary antibody.

3. A kit for the detection of Staphylococcal enterotoxin-B, comprising:

a PVDF surface;

a purified sample of digalactosylceramide;

an antibody which specifically binds to Staphylococcal enterotoxin-B.

4. The kit of claim 3 wherein the digalactosylceramide is prebound to the PVDF surface.

5. The kit of claim 3 wherein the antibody is a polyclonal antiserum.

6. The kit of claim 3 further comprising a sample of Staphylococcal enterotoxin-B for use as a positive control.

7. The kit of claim 3 further comprising a labeled secondary antibody specific for the antibody.

* * * * *